(12) United States Patent
Ebenezer et al.

(10) Patent No.: US 11,183,205 B1
(45) Date of Patent: Nov. 23, 2021

(54) METHODS AND APPARATUS FOR BIOMETRIC PROCESSES

(71) Applicant: Cirrus Logic International Semiconductor Ltd., Edinburgh (GB)

(72) Inventors: Samuel P. Ebenezer, Gilbert, AZ (US); William E. Sherwood, Salt Lake City, UT (US)

(73) Assignee: Cirrus Logic, Inc., Austin, TX (US)

( * ) Notice: Subject to any disclaimer, the term of this patent is extended or adjusted under 35 U.S.C. 154(b) by 0 days.

(21) Appl. No.: 17/074,776

(22) Filed: Oct. 20, 2020

Related U.S. Application Data

(60) Provisional application No. 63/049,219, filed on Jul. 8, 2020.

(51) Int. Cl.
 *G10L 25/51* (2013.01)
 *G06F 21/32* (2013.01)
 *G10L 25/18* (2013.01)
 *H04R 3/04* (2006.01)

(52) U.S. Cl.
 CPC ............ *G10L 25/51* (2013.01); *G06F 21/32* (2013.01); *G10L 25/18* (2013.01); *H04R 3/04* (2013.01)

(58) Field of Classification Search
 None
 See application file for complete search history.

(56) References Cited

U.S. PATENT DOCUMENTS

| | | | | |
|---|---|---|---|---|
| 5,787,187 A | * | 7/1998 | Bouchard | G07C 9/37 382/115 |
| 2008/0262382 A1 | * | 10/2008 | Akkermans | G07C 9/37 600/559 |
| 2009/0061819 A1 | * | 3/2009 | Coughlan | G07C 9/37 455/410 |
| 2018/0376234 A1 | * | 12/2018 | Petrank | H04R 29/001 |
| 2019/0012446 A1 | * | 1/2019 | Lesso | G06F 21/32 |
| 2019/0095653 A1 | * | 3/2019 | Kurosawa | G06F 3/162 |

FOREIGN PATENT DOCUMENTS

| WO | 2007034371 A2 | 3/2007 |
|---|---|---|
| WO | 2016151193 A1 | 9/2016 |

OTHER PUBLICATIONS

International Search Report and Written Opinion of the International Searching Authority, International Application No. PCT/GB2021/051301, dated Aug. 25, 2021.

* cited by examiner

*Primary Examiner* — Paul W Huber
(74) *Attorney, Agent, or Firm* — Jackson Walker L.L.P.

(57) ABSTRACT

A method for generating an acoustic stimulus for use in an ear biometric process on a user, the method comprising: receiving an indication of stimulation frequencies for use in the ear biometric process; grouping the stimulation frequencies into bands of a psychoacoustic scale; generating the acoustic stimulus, the acoustic stimulus comprising a masked bandpass component within each band of the psychoacoustic scale that comprises one or more of the stimulation frequencies.

20 Claims, 13 Drawing Sheets

METHODS AND APPARATUS FOR BIOMETRIC PROCESSES

The present disclosure claims priority to U.S. Provisional Patent Application Ser. No. 63/049,219, filed Jul. 8, 2020, which is incorporated by reference herein in its entirety.

TECHNICAL FIELD

Embodiments of the present disclosure relate to methods, apparatus and systems for biometric processes, and in particular for generating acoustic stimuli for use in biometric processes.

BACKGROUND

It is known that the acoustic properties of a user's ear, whether the outer parts (known as the pinna or auricle), the ear canal or both, differ substantially between individuals and can therefore be used as a biometric to identify the user. One or more loudspeakers or similar transducers positioned close to or within the ear generate an acoustic stimulus, and one or more microphones or other transducers similarly positioned close to or within the ear detect the acoustic response of the ear to the acoustic stimulus. The response may be an ear canal impulse response (ECIR) or an ear canal frequency response (ECFR). One or more features may be extracted from the response signal and used to characterize an individual.

For example, the ear canal is a resonant system, and therefore one feature which may be extracted from the response signal is the impulse response or frequency response of the ear canal (ECIR or ECFR). If the measured resonant frequency (i.e. in the response signal) differs from a stored resonant frequency for the user, a biometric algorithm coupled to receive and analyse the response signal may return a negative result. Other features of the response signal may be similarly extracted and used to characterize the individual. For example, the features may comprise one or more mel frequency cepstrum coefficients. More generally, the transfer function between the acoustic stimulus and the measured response signal (or features of the transfer function) may be determined and compared to a stored transfer function (or stored features of the transfer function) which is characteristic of the user.

One problem associated with ear biometric systems is that the signal to noise ratio of the measured response signal is typically quite low as the biometric features of the signal are relatively weak. This problem can be exacerbated depending on a number of factors. For example, the user may be present in a noisy environment. For example, earphones used to acquire the ear biometric data may be poorly fitted to the user's ear (e.g. inserted too far into the user's ear, or not sufficiently inserted). For example, the user may be generating noise in the canal or headset due to own voice, chewing sounds and handling of the headset. To improve signal-to-noise ratio and to ensure as many frequency modes as possible of ear canals of a population group are excited, probe signals for biometrics typically comprise white noise. However, white noise tends to be perceptually unpleasant to the human ear.

SUMMARY

Embodiments of the present disclosure aim to address or at least ameliorate one or more of the above issues through the construction and/or generation of a probe signal or acoustic stimulus which is both spectrally rich and relatively pleasing to the human ear, when compared to white noise. Embodiments of the present disclosure aim to harness the effect of psychoacoustic masking to embed acoustic content at frequencies which are pertinent for use in biometric processes in an acoustic stimulus that is pleasing to the ear.

According to a first aspect of the disclosure, there is provided a method for generating an acoustic stimulus for use in an ear biometric process on a user, the method comprising: receiving an indication of stimulation frequencies for use in the ear biometric process; grouping the stimulation frequencies into bands of a psychoacoustic scale; generating the acoustic stimulus, the acoustic stimulus comprising a masked bandpass component within each band of the psychoacoustic scale that comprises one or more of the stimulation frequencies.

The indication of frequencies may be extracted from a model generated from one or more ear canal frequency responses. The model may be a generic model generated from an analysis of ear canal frequency responses from a subset of the general population. Alternatively, the model may be a user-specific model generated from an analysis of an ear canal frequency response of the user. Accordingly, the ear canal frequency response of the user may be obtained during a biometric enrolment process performed on the user.

In some embodiments, frequencies in the indication of frequencies may align with ear canal acoustic modes in the one or more ear canal frequency responses.

The psychoacoustic scale may be a bark scale or an equivalent rectangular bandwidth, ERB, scale or a mel scale or a logarithmic scale or an octave scale. The psychoacoustic scale may comprise a scale of frequencies judged by a human listener to be substantially equal in distance from one another.

The acoustic stimulus may further comprise one or more adjacent masked bandpass components within adjacent bands of the psychoacoustic scale. The adjacent bands may be adjacent to bands of the psychoacoustic scale that comprises one or more of the stimulation frequencies. Each of the one or more adjacent masked bandpass components may temporally overlap a respective one of the masked bandpass components to which they are adjacent.

The method may further comprise determining a time duration for each of the masked bandpass components. In some embodiments, the time duration is determined for each of the masked bandpass components based on an ambient noise level in a microphone signal used in the ear biometric process. Additionally or alternatively, the time duration may be determined for each of the masked bandpass components based on the ambient noise level in a respective band of the psychoacoustic scale.

Two or more of the masked bandpass components may be temporally ordered with respect to each other. In some embodiments, the method may comprise temporally ordering the masked bandpass components or varying a temporal order to reduce perceptual intrusiveness of the acoustic stimulus to a user.

In some embodiments, generating the acoustic stimulus may comprise: generating each of the masked bandpass components and combining the masked band pass components to generate the acoustic stimulus.

The method of any one of the preceding claims, further comprising determining a signal level of each of the masked bandpass components based on one or more of: a) an expected signal-to-noise ratio (SNR); b) a measured ambient noise level; c) a spectral shape of ambient background noise;

d) a measured level of noise leakage into an ear canal of the user; and e) playback signal information.

The method may further comprise combining the acoustic stimulus with a comfort stimulus. The comfort stimulus may comprise one or more of: a) one or more random tones; b) music; c) one or more triad progressions; and d) one or more arpeggios. The comfort stimulus may comprise a playback signal comprising one or more of: a) a voice call signal; b) a hearing augmentation signal; c) a passthrough audio signal; and d) an audio signal notifying the user when a device is placed in or on the user's ear.

The method may further comprise adding additional noise, such as white noise to one or more of the determined psychoacoustic bands.

The method may further comprise applying the acoustic stimulus to the ear canal of a user.

According to another aspect of the disclosure, there is provided a non-transitory machine-readable medium storing instructions which, when executed by one or more processors, cause an electronic apparatus to perform the method as described above.

According to another aspect of the disclosure, there is provided an apparatus comprising processing circuitry and a non-transitory machine-readable medium storing instructions which, when executed by the processing circuitry, cause the apparatus to: receive an indication of stimulation frequencies for use in the ear biometric process; group the stimulation frequencies into bands of a psychoacoustic scale; generate the acoustic stimulus, the acoustic stimulus comprising a masked bandpass component within each band of the psychoacoustic scale that comprises one or more of the stimulation frequencies.

The indication of frequencies may be extracted from a model generated from one or more ear canal frequency responses. The model may be a generic model generated from an analysis of ear canal frequency responses from a subset of the general population. Alternatively, the model may be a user-specific model generated from an analysis of an ear canal frequency response of the user. Accordingly, the ear canal frequency response of the user may be obtained during a biometric enrolment process performed on the user.

In some embodiments, frequencies in the indication of frequencies may align with ear canal acoustic modes in the one or more ear canal frequency responses.

The psychoacoustic scale may be a bark scale or an equivalent rectangular bandwidth, ERB, scale or a mel scale or a logarithmic scale or an octave scale. The psychoacoustic scale may comprise a scale of frequencies judged by a human listener to be substantially equal in distance from one another.

The acoustic stimulus may further comprise one or more adjacent masked bandpass components within adjacent bands of the psychoacoustic scale. The adjacent bands may be adjacent to bands of the psychoacoustic scale that comprises one or more of the stimulation frequencies. Each of the one or more adjacent masked bandpass components may temporally overlap a respective one of the masked bandpass components to which they are adjacent.

The instructions may further cause the apparatus to determine a time duration for each of the masked bandpass components. In some embodiments, the time duration is determined for each of the masked bandpass components based on an ambient noise level in a microphone signal used in the ear biometric process. Additionally or alternatively, the time duration may be determined for each of the masked bandpass components based on the ambient noise level in a respective band of the psychoacoustic scale.

Two or more of the masked bandpass components may be temporally ordered with respect to each other. In some embodiments, the instructions may further cause the apparatus to temporally order the masked bandpass components or vary a temporal order to reduce perceptual intrusiveness of the acoustic stimulus to a user.

In some embodiments, generating the acoustic stimulus may comprise: generating each of the masked bandpass components and combining the masked band pass components to generate the acoustic stimulus.

The instructions may further cause the apparatus to determine a signal level of each of the masked bandpass components based on one or more of: a) an expected signal-to-noise ratio (SNR); b) a measured ambient noise level; c) a spectral shape of ambient background noise; d) a measured level of noise leakage into an ear canal of the user; and e) playback signal information.

The instructions may further cause the apparatus to combine the acoustic stimulus with a comfort stimulus. The comfort stimulus may comprise one or more of: a) one or more random tones; b) music; c) one or more triad progressions; and d) one or more arpeggios. The comfort stimulus may comprise a playback signal comprising one or more of: a) a voice call signal; b) a hearing augmentation signal; c) a passthrough audio signal; and d) an audio signal notifying the user when a device is placed in or on the user's ear.

The instructions may further cause the apparatus to add additional noise, such as white noise to one or more of the determined psychoacoustic bands.

The instructions may further cause the apparatus to apply the acoustic stimulus to the ear canal of a user.

According to another aspect of the disclosure, there is provided an electronic device comprising the apparatus as described above.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of non-limiting examples with reference to the drawings, in which.

DESCRIPTION OF EMBODIMENTS

Embodiments of the disclosure relate to methods, apparatus and systems for biometric processes, and particularly to methods, apparatus and systems for improving biometric processes involving the measured response of a user's ear to an acoustic stimulus.

Figure 1A:
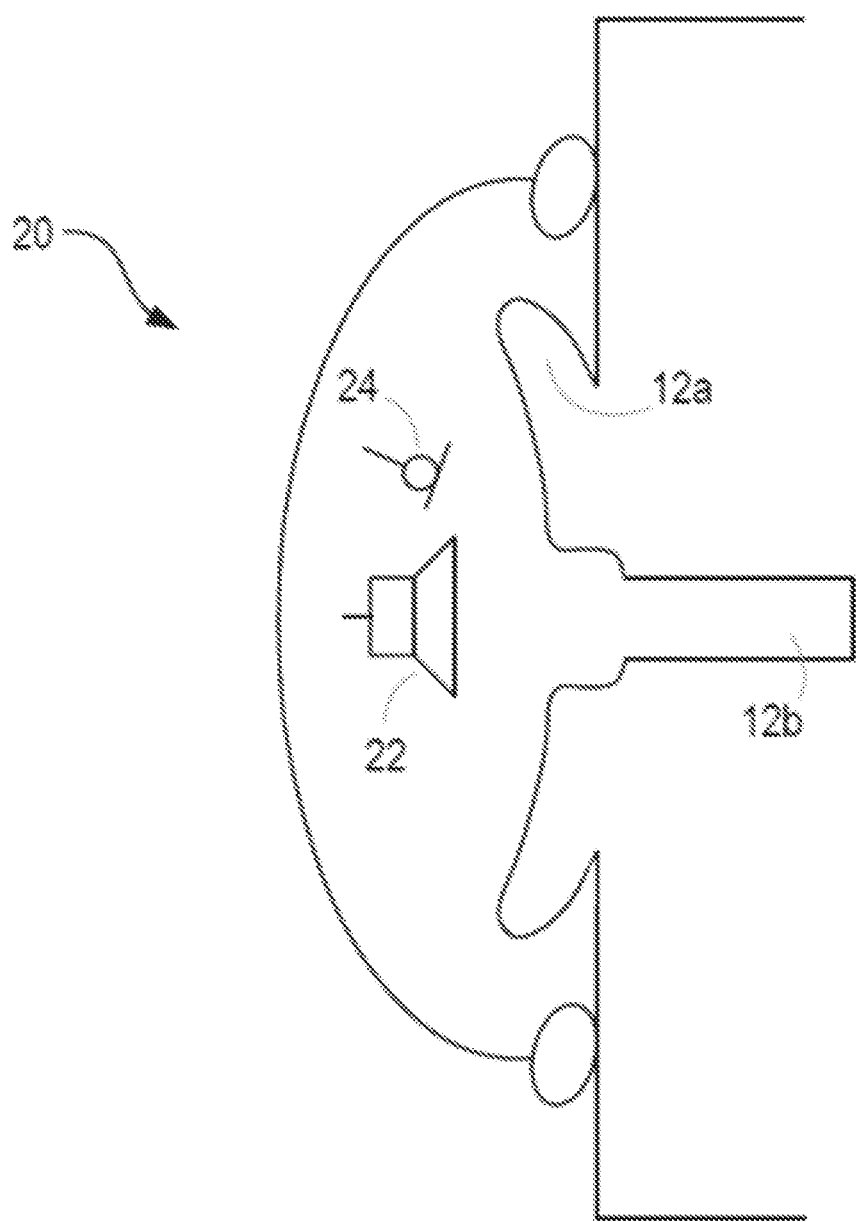
FIGS. 1a to 1e show examples of personal audio devices.

FIG. 1a shows a schematic diagram of a user's ear, comprising the (external) pinna or auricle 12a, and the (internal) ear canal 12b. A personal audio device 20 comprising a circum-aural headphone is worn by the user over the ear. The headphone comprises a shell which substantially surrounds and encloses the auricle 12a, so as to provide a physical barrier between the user's ear and the external environment. Cushioning or padding may be provided at an edge of the shell, so as to increase the comfort of the user, and also the acoustic coupling between the headphone and the user's skin (i.e. to provide a more effective barrier between the external environment and the user's ear).

The headphone comprises one or more loudspeakers 22 positioned on an internal surface of the headphone and arranged to generate acoustic signals towards the user's ear and particularly the ear canal 12b. The headphone further comprises one or more microphones 24, also positioned on the internal surface of the headphone, arranged to detect acoustic signals within the internal volume defined by the headphone, the auricle 12a and the ear canal 12b.

The headphone may be able to perform active noise cancellation, to reduce the amount of noise experienced by the user of the headphone. Active noise cancellation operates by detecting a noise (i.e. with a microphone) and generating a signal (i.e. with a loudspeaker) that has the same amplitude as the noise signal but is opposite in phase. The generated signal thus interferes destructively with the noise and so lessens the noise experienced by the user. Active noise cancellation may operate on the basis of feedback signals, feedforward signals, or a combination of both. Feedforward active noise cancellation utilizes one or more microphones on an external surface of the headphone, operative to detect the environmental noise before it reaches the user's ear. The detected noise is processed quickly, and the cancellation signal generated so as to match the incoming noise as it arrives at the user's ear. Feedback active noise cancellation utilizes one or more error microphones positioned on the internal surface of the headphone, operative to detect the combination of the noise and the audio playback signal generated by the one or more loudspeakers. This combination is used in a feedback loop, together with knowledge of the audio playback signal, to adjust the cancelling signal generated by the loudspeaker and so reduce the noise. The microphone 24 shown in FIG. 1a may therefore form part of an active noise cancellation system, for example, as an error microphone.

Figure 1B:
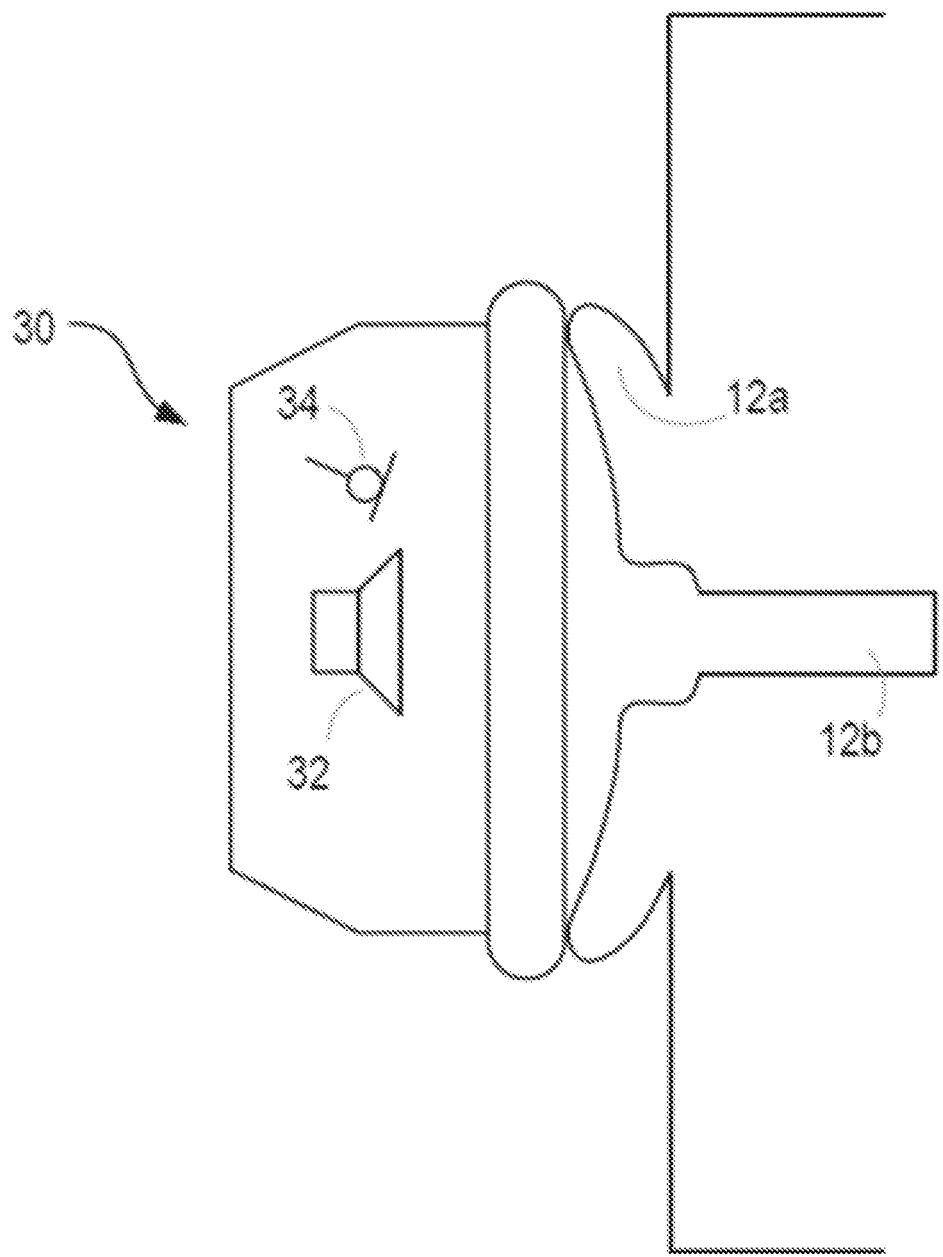

FIG. 1b shows an alternative personal audio device 30, comprising a supra-aural headphone. The supra-aural headphone does not surround or enclose the user's ear, but rather sits on the auricle 12a. The headphone may comprise a cushion or padding to lessen the impact of environmental noise. As with the circum-aural headphone shown in FIG. 1a, the supra-aural headphone comprises one or more loudspeakers 32 and one or more microphones 34. The loudspeaker(s) 32 and the microphone(s) 34 may form part of an active noise cancellation system, with the microphone 34 serving as an error microphone.

Figure 1C:
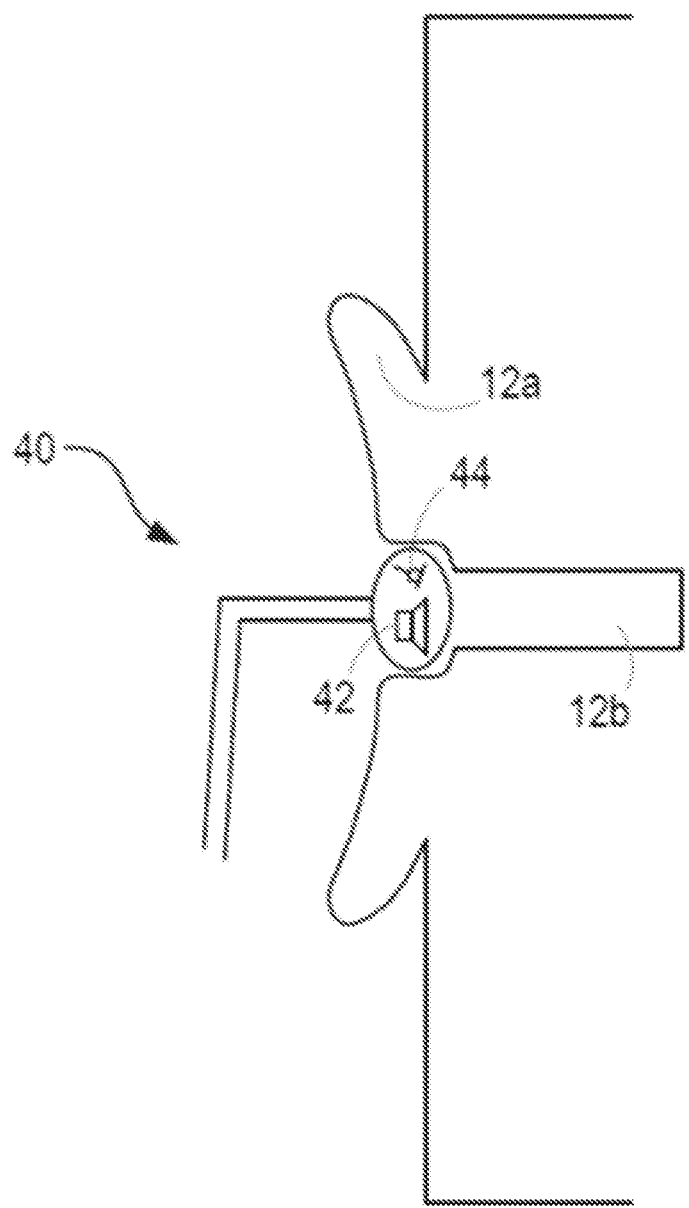

FIG. 1c shows a further alternative personal audio device 40, comprising an intra-concha headphone (or earphone). In use, the intra-concha headphone sits inside the user's concha cavity. The intra-concha headphone may fit loosely within the cavity, allowing the flow of air into and out of the user's ear canal 12b.

As with the devices shown in FIGS. 1a and 1b, the intra-concha headphone comprises one or more loudspeakers 42 and one or more microphones 44, which may form part of an active noise cancellation system.

Figure 1D:
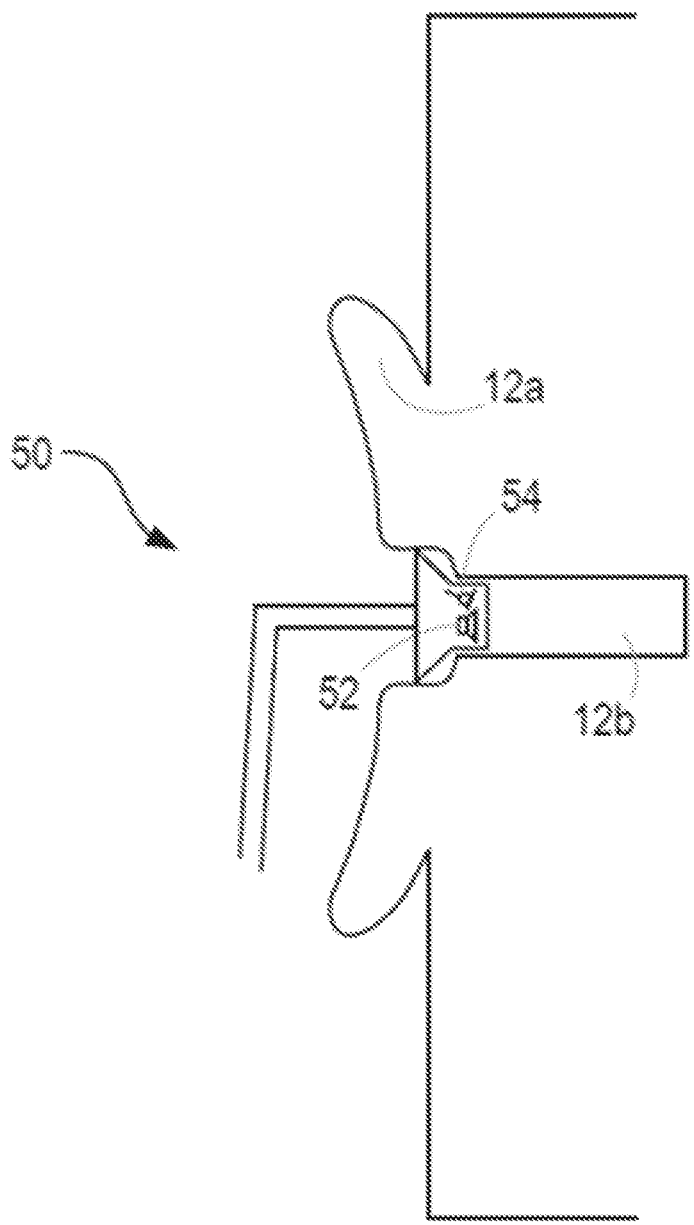

FIG. 1d shows a further alternative personal audio device 50, comprising an in-ear headphone (or earphone), insert headphone, or ear bud. This headphone is configured to be partially or totally inserted within the ear canal 12b and may provide a relatively tight seal between the ear canal 12b and the external environment (i.e. it may be acoustically closed or sealed). The headphone may comprise one or more loudspeakers 52 and one or more microphones 54, as with the other devices described above, and these components may form part of an active noise cancellation system.

As the in-ear headphone may provide a relatively tight acoustic seal around the ear canal 12b, external noise (i.e. coming from the environment outside) detected by the microphone 54 is likely to be low.

Figure 1E:
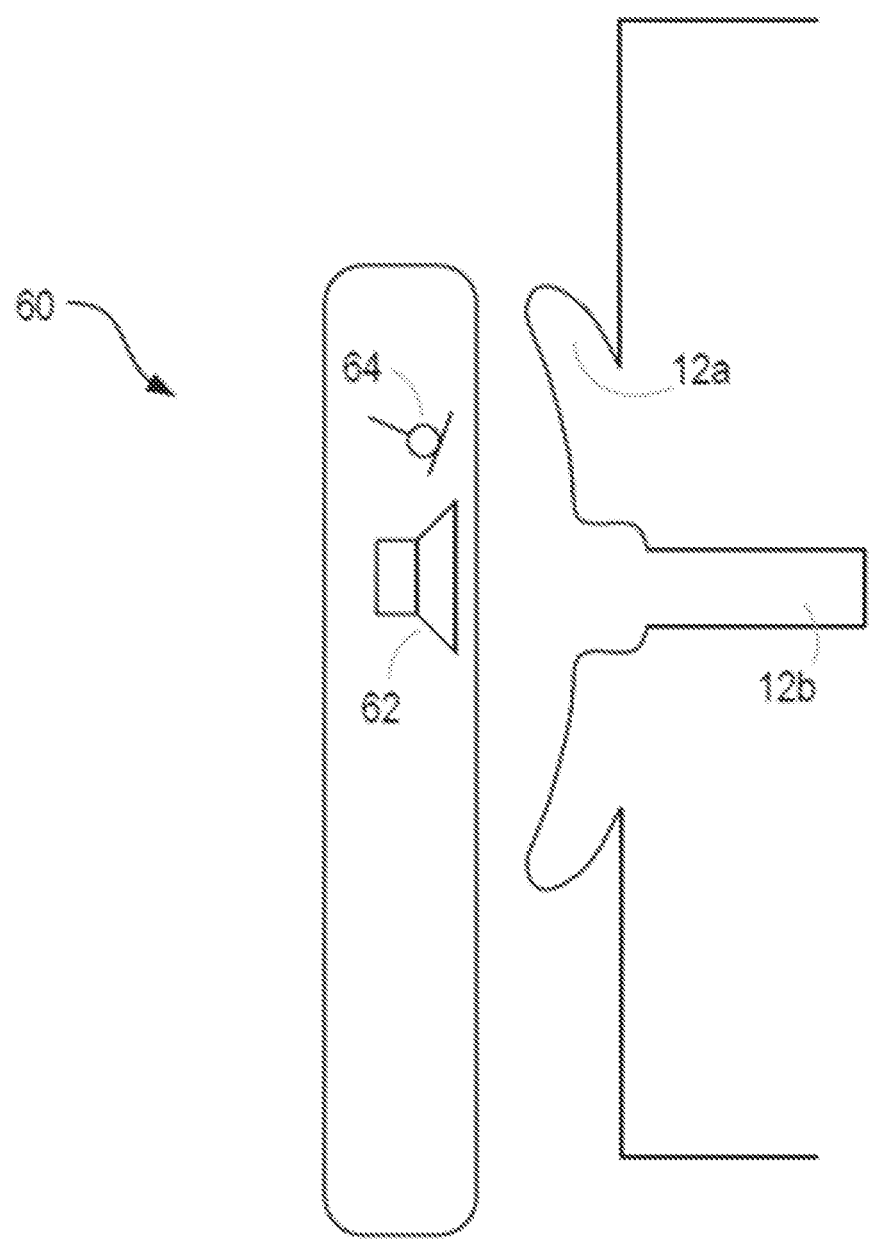

FIG. 1e shows a further alternative personal audio device 60, which is a mobile or cellular phone or handset. The handset 60 comprises one or more loudspeakers 62 for audio playback to the user, and one or more microphones 64 which are similarly positioned.

In use, the handset 60 is held close to the user's ear so as to provide audio playback (e.g. during a call). While a tight acoustic seal is not achieved between the handset 60 and the user's ear, the handset 60 is typically held close enough that an acoustic stimulus applied to the ear via the one or more loudspeakers 62 generates a response from the ear which can be detected by the one or more microphones 64. As with the other devices, the loudspeaker(s) 62 and microphone(s) 64 may form part of an active noise cancellation system.

All of the personal audio devices described above thus provide audio playback to a single user in use. Each device comprises one or more loudspeakers and one or more microphones, which may be utilized to generate biometric data related to the frequency response of the user's ear. The loudspeaker is operable to generate an acoustic stimulus, or acoustic probing wave, towards the user's ear, and the microphone is operable to detect and measure a response of the user's ear to the acoustic stimulus, e.g. to measure acoustic waves reflected from the ear canal or the pinna. The acoustic stimulus may be sonic (for example in the audio frequency range of say 20 Hz to 20 kHz) or ultra-sonic (for example greater than 20 kHz or in the range 20 kHz to 50 kHz) or near-ultrasonic (for example in the range 15 kHz to 25 kHz) or subsonic in frequency. In some examples the microphone signal may be processed to measure received signals of the same frequency as that transmitted.

Another biometric marker may comprise otoacoustic noises emitted by the cochlear in response to the acoustic stimulus waveform. The otoacoustic response may comprise a mix of the frequencies in the input waveform. For example, if the input acoustic stimulus consists of two tones at frequencies f1 and f2, the otoacoustic emission may include a component at frequency 2*f1-f2. The relative power of frequency components of the emitted waveform has been shown to be a useful biometric indicator. In some examples therefore the acoustic stimulus may comprise tones of two or more frequencies and the amplitude of mixing products at sums or differences of integer-multiple frequencies generated by otoacoustic emissions from the cochlear may be measured. Alternatively, otoacoustic emissions may be stimulated and measured by using stimulus waveforms comprising fast transients, e.g. clicks.

Depending on the construction and usage of the personal audio device, the measured response may comprise user-specific components, i.e. biometric data relating to the auricle 12a, the ear canal 12b, or a combination of both the auricle 12a and the ear canal 12b. For example, the circumaural headphones shown in FIG. 1a will generally acquire data relating to the auricle 12a and potentially also the ear canal 12b. The insert headphones shown in FIG. 1d will generally acquire data relating only to the ear canal 12b.

One or more of the personal audio devices described above (or rather, the microphones within those devices) may be operable to detect bone-conducted voice signals from the user. That is, as the user speaks, sound is projected away from the user's mouth through the air. However, acoustic vibrations will also be carried through part of the user's skeleton or skull, such as the jawbone. These vibrations may be coupled to the ear canal 12b through the jaw or some other part of the user's skeleton or skull and detected by the microphone. Lower frequency sounds tend to experience a stronger coupling than higher frequency sounds, and voiced speech (i.e. that speech or those phonemes generated while the vocal cords are vibrating) is coupled more strongly via bone conduction than unvoiced speech (i.e. that speech or those phonemes generated while the vocal cords are not vibrating). The in-ear headphone 50 may be particularly suited to detecting bone-conducted speech owing to the tight acoustic coupling around the ear canal 12b.

All of the devices shown in FIGS. 1a to 1e and described above may be used to implement aspects of the disclosure.

Figure 2:
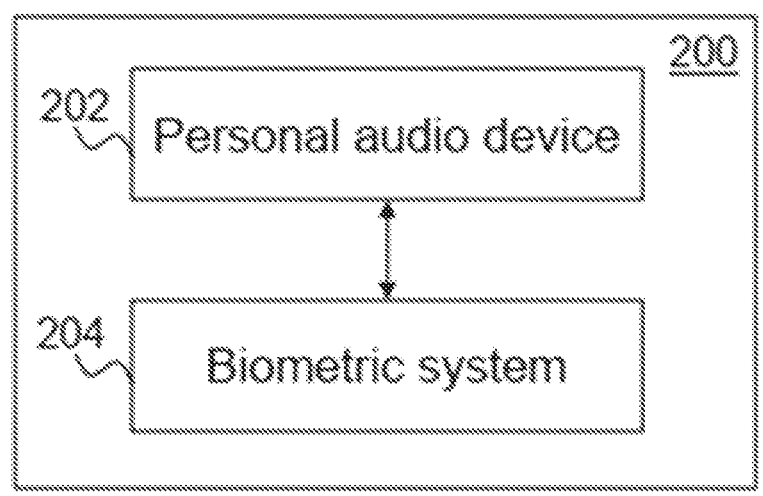
FIG. 2 shows an arrangement according to embodiments of the disclosure.

FIG. 2 shows an arrangement 200 according to embodiments of the disclosure. The arrangement 200 comprises a personal audio device 202 and a biometric system 204. The personal audio device 202 may be any device which is suitable for, or configurable to provide audio playback to a single user. The personal audio device 202 generally comprises one or more loudspeakers, and one or more microphones which, in use, are positioned adjacent to or within a user's ear. The personal audio device 202 may be wearable and comprise headphones for each of the user's ears. Alternatively, the personal audio device 202 may be operable to be carried by the user and held adjacent to the user's ear or ears during use. The personal audio device 202 may comprise headphones or a mobile phone handset, as described above with respect to any of FIGS. 1a to 1 *e*.

The biometric system 204 is coupled to the personal audio device 202 and operative to control the personal audio device 202 to acquire biometric data which is indicative of the individual using the personal audio device 202.

The personal audio device 202 thus generates an acoustic stimulus for application to the user's ear and detects or measures the response of the ear to the acoustic stimulus. For example, the acoustic stimulus may be in the sonic range, or ultra-sonic. In some embodiments, the acoustic stimulus may have a flat frequency spectrum over a relevant frequency range or be pre-processed in such a way that those frequencies that allow for a good discrimination between individuals are emphasized (i.e. have a higher amplitude than other frequencies). The measured response corresponds to the reflected signal received at the one or more microphones, with certain frequencies being reflected at higher amplitudes than other frequencies owing to the particular response of the user's ear.

The biometric system 204 may send suitable control signals to the personal audio device 202, so as to initiate the acquisition of biometric data, and receive data from the personal audio device 202 corresponding to the measured response. The biometric system 204 is operable to extract one or more features from the measured response and utilize those features as part of a biometric process.

Some examples of suitable biometric processes include biometric enrolment and biometric authentication. Enrolment comprises the acquisition and storage of biometric data which is characteristic of an individual. In the present context, such stored data may be known as an "ear print". Authentication (sometimes referred to as verification) comprises the acquisition of biometric data from an individual, and the comparison of that data to the stored ear prints of one or more enrolled or authorised users. A positive comparison (i.e. a determination that the acquired data matches or is sufficiently close to a stored ear print) results in the individual being authenticated. For example, the individual may be permitted to carry out a restricted action, or granted access to a restricted area or device. A negative comparison (i.e. a determination that the acquired data does not match or is not sufficiently close to a stored ear print) results in the individual not being authenticated. For example, the individual may not be permitted to carry out the restricted action or granted access to the restricted area or device.

According to embodiments of the disclosure, the personal audio device 202 is further operable to determine whether a signal to noise ratio (SNR) of the response signal is adequate for performing a biometric process, such as feature extraction for authentication. In response to determining that the SNR of the response signal is inadequate, the personal audio device 202 may be operable to modify one or more properties of the acoustic stimulus to improve the SNR of the response signal, as discussed in more detail below.

The biometric system 204 may, in some embodiments, form part of the personal audio device 202 itself. Alternatively, the biometric system 204 may form part of an electronic host device (e.g. an audio player) to which the personal audio device 202 is coupled, through wires or wirelessly. In yet further embodiments, operations of the biometric system 204 may be distributed between circuitry in the personal audio device 202 and the electronic host device.

Figure 3:
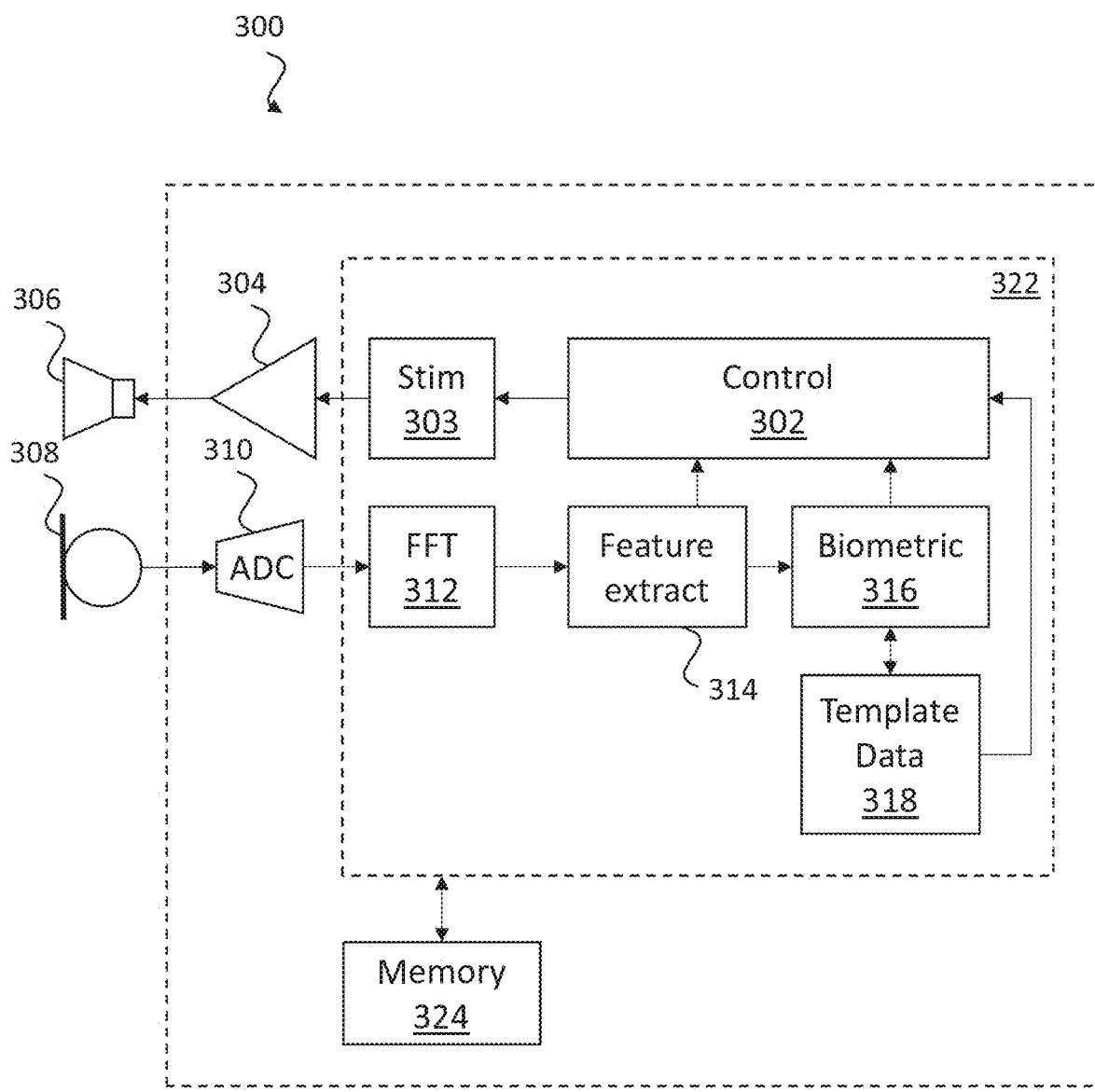
FIG. 3 shows a system according to embodiments of the disclosure.

FIG. 3 shows a system 300 according to embodiments of the disclosure.

The system 300 comprises processing circuitry 322, which may comprise one or more processors, such as a central processing unit or an applications processor (AP), or a digital signal processor (DSP).

The one or more processors may perform methods as described herein on the basis of data and program instructions stored in memory 324. Memory 324 may be provided as a single component or as multiple components or co-integrated with at least some of processing circuitry 322. Specifically, the methods described herein can be performed in processing circuitry 322 by executing instructions that are stored in non-transient form in the memory 324, with the program instructions being stored either during manufacture of the system 300 or personal audio device 202 or by upload while the system or device is in use.

The processing circuitry 322 comprises a stimulus generator module 303 which is coupled directly or indirectly to an amplifier 304, which in turn is coupled to a loudspeaker 306.

The stimulus generator module 303 generates an electrical audio signal and provides the electrical audio signal to the amplifier 304, which amplifies it and provides the amplified signal to the loudspeaker 306. The loudspeaker 306 generates a corresponding acoustic signal which is output to the user's ear (or ears). The audio signal may be sonic or ultra-sonic, for example. The audio signal may have a flat frequency spectrum or be pre-processed in such a way that those frequencies that allow for a good discrimination between individuals are emphasized (i.e. have a higher amplitude than other frequencies).

As noted above, the audio signal may be output to all or a part of the user's ear (i.e. the auricle 12a or the ear canal 12b). The audio signal is reflected off the ear, and the reflected signal (or echo signal) is detected and received by a microphone 308. The reflected signal thus comprises data, which is characteristic of the individual's ear, and suitable for use as a biometric.

The reflected signal is passed from the microphone 308 to an analogue-to-digital converter (ADC) 310, where it is converted from the analogue domain to the digital domain. Of course, in alternative embodiments the microphone 308 may be a digital microphone and produce a digital data signal (which does not therefore require conversion to the digital domain).

The signal is detected by the microphone 308 in the time domain. The features extracted for the purposes of the biometric process may be in the time domain. However, in some embodiments, the features extracted for the purposes of the biometric process may be in the frequency domain (in that it is the frequency response of the user's ear which is characteristic). The system 300 may therefore comprise a Fourier transform module 312, which converts the reflected signal to the frequency domain. For example, the Fourier transform module 312 may implement a fast Fourier transform (FFT).

The system 300 may further comprise a microphone 330, and an associated analogue-to-digital converter (ADC) 332 where necessary. The microphone 330 may be an external or out-of-ear microphone, which may be used for noise signal determinations, for example, as discussed in more detail below.

The transformed signal is then passed to a feature extract module 314, which extracts one or more features of the transformed signal for use in a biometric process (e.g. biometric enrolment, biometric authentication, etc). For example, the feature extract module 314 may extract the resonant frequency of the user's ear. For example, the feature extract module 314 may extract one or more mel frequency cepstrum coefficients. Alternatively, the feature extract module 314 may determine the frequency response of the user's ear at one or more predetermined frequencies, or across one or more ranges of frequencies.

The extracted feature(s) are passed to a biometric module 316, which performs a biometric process on them. For example, the biometric module 316 may perform a biometric enrolment, in which the extracted features (or parameters derived therefrom) are stored as part of biometric template data 318 which is characteristic of the individual (i.e. as an ear print). The biometric template data 318 may be stored within the system 300 or remote from the system 300 (and accessible securely by the biometric module 316). In another example, the biometric 316 may perform a biometric authentication, and compare the one or more extract features to corresponding features stored in the biometric template data 318 (or multiple stored template ear prints). The biometric template data 318 may comprise template data or ear prints of enrolled users. Additionally or alternatively the biometric template data 318 may comprise data representing multiple users, for example a subset of the general population. This template data 318 may also be accessible by the control module 302 for use in generating an acoustic stimulus as is described in more detail below.

The biometric module 316 may generate a biometric result (which may be the successful or unsuccessful generation of an ear print, as well as successful or unsuccessful authentication) and outputs the result to control module 302.

Thus in some embodiments the feature extract module 314 may be designed with foreknowledge of the nature of the stimulus, for example knowing the spectrum of the applied stimulus signal, so that the response or transfer function may be appropriately normalised. In other embodiments the feature extract module 314 may comprise a second input (not shown) to monitor the stimulus and hence provide the feature extract module 314 with information about the stimulus signal or its spectrum so that the feature extract module 314 may calculate the transfer function from the stimulus waveform stimulus to received acoustic waveform from which it may derive the desired feature parameters. In the latter case, the stimulus signal may also pass to the feature extract module 314 via the FFT module 312.

It will be appreciated that the stimulus waveforms applied to the ear for biometric purposes tend to comprise spectrally rich white noise having a substantially flat frequency response. White noise applied to an ear canal has the effect of exciting most of all resonant modes of the ear canal, which in turn leads to a more complete ear canal impulse response across a larger frequency spectrum. A problem with white noise, however, is that it is not typically pleasant or pleasing to the human ear. In many cases, in fact, white noise is very displeasing to humans.

Embodiments of the present disclosure aim to generate an acoustic stimulus which has the effect of exciting multiple modes of the ear canal of a user, whilst not being unpleasant to the human ear when applied to the ear canal of a user. Embodiments of the present disclosure thus aim to provide a psycho-acoustic probe signal that is spectrally rich. It is thus proposed to generate a signal comprising multiple tones in addition to embedded masked content (e.g. masked by the tones), as will be described in more detail below.

Taking the above into consideration, the control module 302 is configured to control the stimulus generator module 303 to generate an acoustic stimulus having the properties described above. The control module receives biometric template data 318 and controls the stimulus generator module 303 to generate an acoustic stimulus having the desired properties.

In some embodiments the stimulus generator 303 may be configurable to apply playback such as music to the loudspeaker 306, e.g. normal playback operation. The feature extract module may be configurable to extract the response or transfer function from whatever signal components the stimulus waveform contains.

Figure 4:
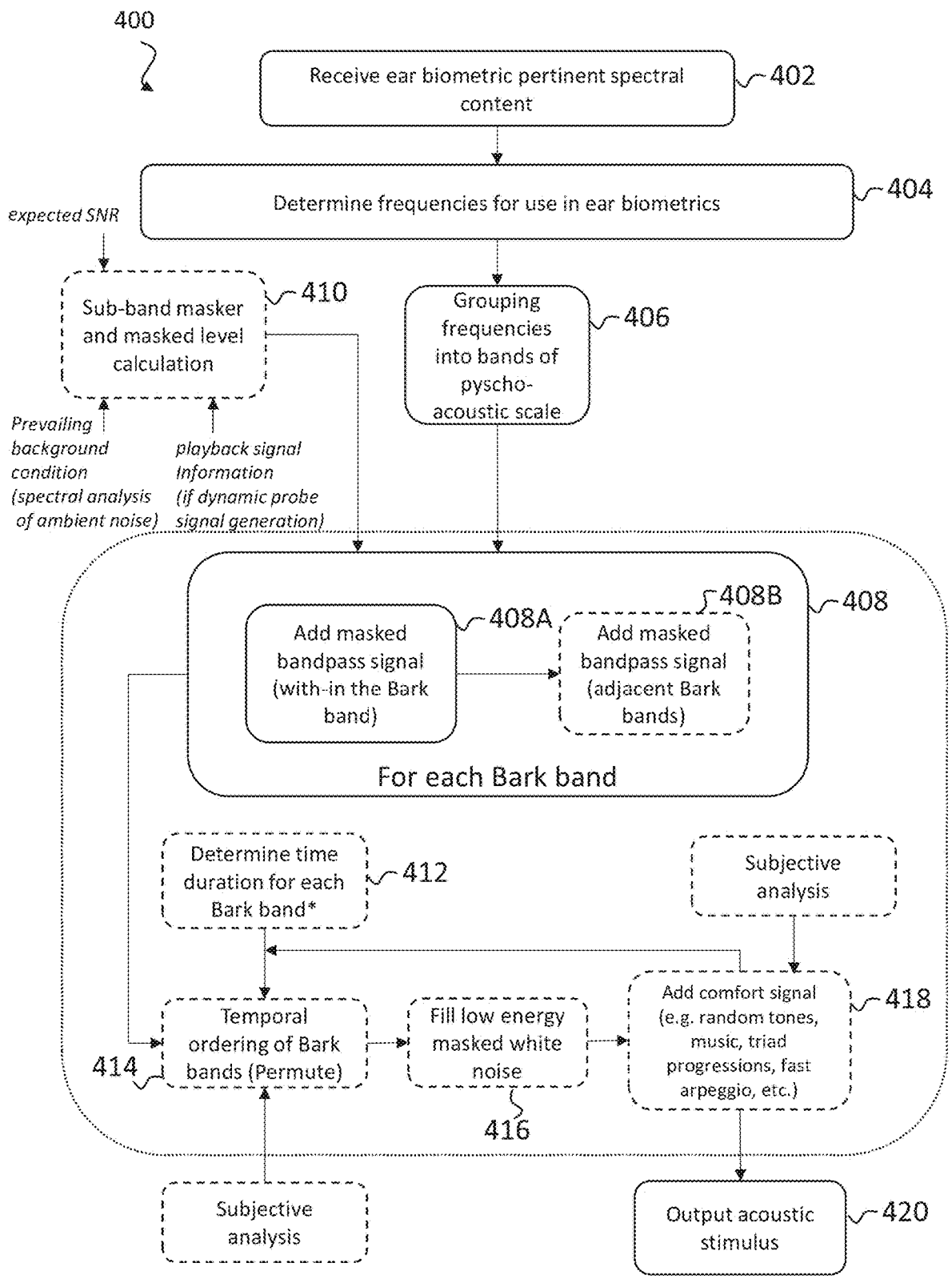
FIG. 4 illustrates a process according to embodiments of the disclosure.

FIG. 4 is a block diagram of a process 400 for generate an acoustic probe according to embodiments of the present disclosure, where optional steps of the process 400 are denoted with broken lines. It will be understood that the order of steps described in the process 400 below may be changed and methods for determining various results described below may be varied without departing from the scope of the disclosure. For context, the process 400 is described below as being implemented by the system 300 shown in FIG. 3. In other embodiments, however, the process 400 may be implemented in another system (not shown) which may be proximate to or remote from the system 300. For example, the process 400 may be implemented in the cloud. The generated acoustic stimulus may be used by the system 300 or other systems for use in a biometric process, such as biometric enrolment or authentication, an example of which is described above. For example, where a user has multiple personal audio devices, the acoustic stimulus by the process 400 may be utilised by each of those devices for one or more biometric processes. Various steps of the process 400 described below may be implemented by different modules of the system 300 or other systems which may themselves be disparate from one another.

At step 402, the control module 302 may obtain ear biometric pertinent spectral content. Ear biometric pertinent spectral content may comprise biometric template data 318 as described above. For example, the control module 302 may receive biometric template data 318 pertaining to one or more human ear prints which may be from enrolled users of the system 300, or from the general population or a mixture of both. The biometric template data 318 may comprise a model generated from one or more ear canal frequency responses, again of enrolled users and/or from the general population. As such, the model may, in some embodiments, be user-specific. For example, the model may be generated during biometric enrolment of a user, as is described in detail above.

At step 404, the control module 302 may receive, or generate from the received ear biometric pertinent spectral content, an indication of frequencies useful in performing one or more biometric processes, such as biometric enrolment or authentication. Such frequencies may align with ear canal acoustic modes in the biometric template data 318. These ear canal acoustic modes may be of the general population or may be user-specific, or both. Application of an acoustic probe having components at such frequencies may illicit a particularly strong response at those each canal acoustic modes, thereby improving the ear canal response signal for use in one or more biometric processes.

Figure 5A:
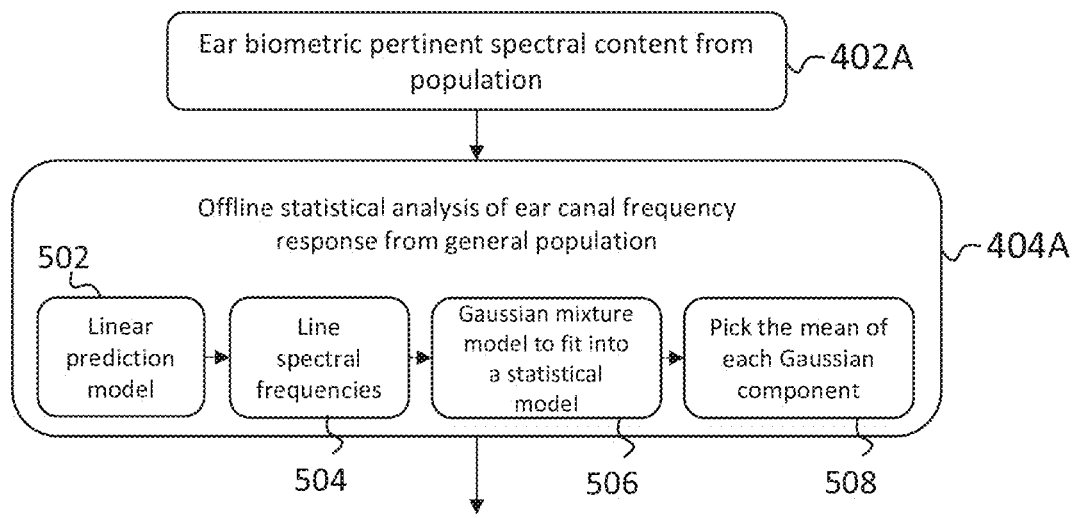
FIGS. 5a and 5b illustrate variations of the process shown in FIG. 4.
Figure 5B:
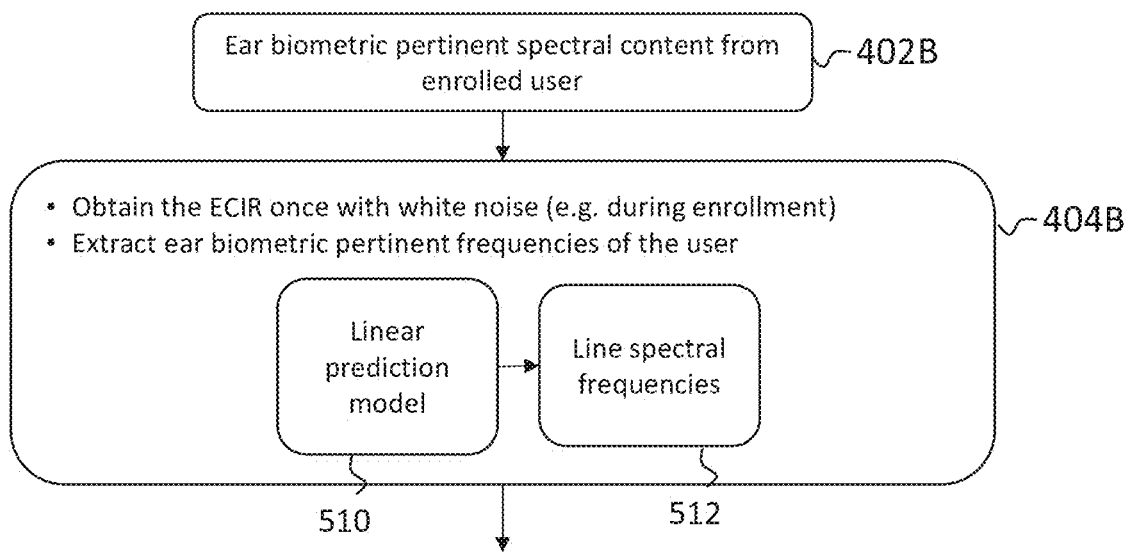

FIGS. 5a and 5b provide two alternative implementations of steps 402 and 404 of FIG. 4.

FIG. 5a relates to an implementation in which the received spectral content relates to a subset of the general population. FIG. 5b relates to an implementation in which the received spectral content relates to a specific user, such as an enrolled user of the system 300.

In the implementation in FIG. 5a, at step 402A, ear biometric pertinent spectral content is received which is representative of the general population or a subset of the general population. At step 404A, an analysis may be performed on this received content to generate an indication of frequencies which may be useful in a biometric process. For example, a statistical analysis of the received content may be performed as set out in steps 502 to 508 described below.

At step 502, a linear prediction model is generated based on the spectral content received at step 402A. For example, where the received content is a model of ear canal frequency response, a linear prediction model may be generated on that ear canal frequency response model.

At step 504, line spectral frequencies (LSFs) or line spectral pairs (LSPs) may be generated based on the linear prediction model.

At step 506, a Gaussian mixture model (GMM) or other mixture model may be generated based on the LSFs. For example, the GMM may be generated which substantially fits the line spectral frequency response of the linear prediction model.

In some embodiments, the probability density function (PDF) of the model may be defined as $$p(f) = \sum_{i=1}^{N} w_i \aleph(\mu_i, \sigma_i^2)$$

where p(f) is the PDF as a function of the frequency f, $\aleph(\mu_i, \sigma_i^2)$ is the $i^{th}$ Gaussian component as a function of the frequency f with mean $\mu_i$ and variance $\sigma_i^2$, $w_i$ is the corresponding weight, and N is the number of Gaussian components.

Figure 6:
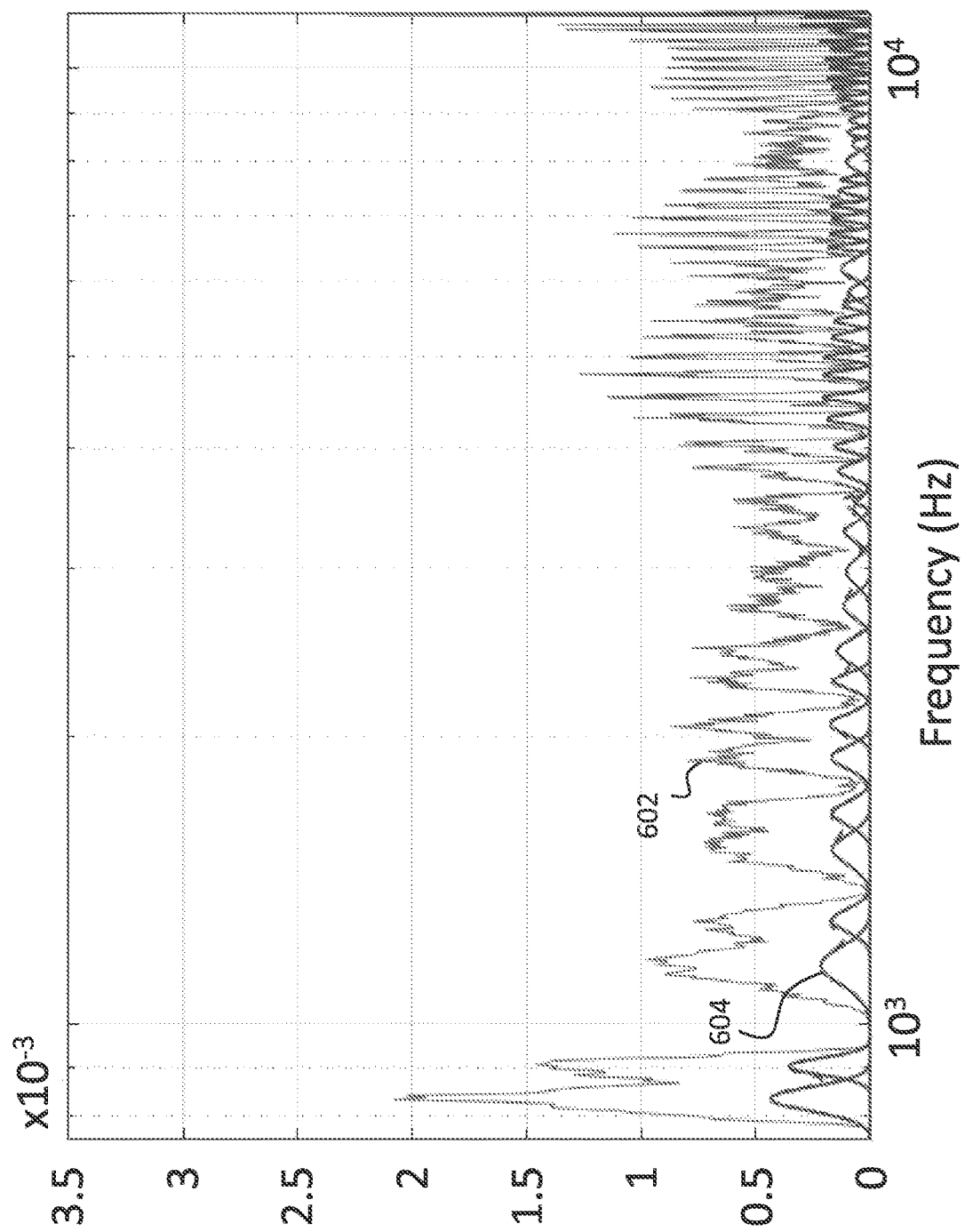
FIG. 6 is a graph representing ear biometric data in various forms.

FIG. 6 graphically illustrates an empirical line spectral frequency distribution 602 obtained from a subset of the general population and a corresponding GMM 604 for a typical ear canal model received by the control module 302 at step 402A. It can be seen that the maxima in the GMM 604 substantially align with peaks in the line spectral frequency response 602. As such, the GMM 604 provides an estimation of a set of frequencies of sound likely to induce ear canal resonance when applied to a human ear of the subset of the general population (or whatever subset has been provided at step 402A).

Referring again to FIG. 5a, at step 508, the GMM 604 is then used to determine the frequencies for use in ear biometrics. In doing so, the frequencies preferably align acoustic modes of the model ear canal frequency response used to generate the GMM 604. In other words, the determined frequencies may substantially align with a set of frequencies that are likely to induce resonance in a human ear canal when applied as an acoustic stimulus by the stimulus generator module. In some embodiments, the determined frequencies may comprise the centre frequency or mean frequency of each Gaussian distribution or peak (or mode) in the GMM 604. In other embodiments, a threshold may be applied to the GMM 604 and/or the line spectral frequency response, and only peaks in GMM 604 corresponding to signal power exceeding that threshold may be used to determine the frequencies for use in the biometric process.

FIG. 5b relates to an implementation in which the received spectral content relates to a specific user, such as an enrolled user of the system 300.

The control module 302 may receive template data 318 at step 402B. The template data 318 may comprise an ear canal response or a model of ear canal response of a user generated over one or more biometric enrolment or authentication processes previously undertaken. Such biometric enrolment process(es) may involve applying a white noise acoustic stimulus or other spectrally rich signal to the ear canal of the specific user to maximise the spectral richness of the ear canal response. The user-specific model or ear canal template may be refined over time during successive biometric processes performed by the system 300 or other systems on the user.

In a similar manner to that described above with reference to FIG. 5a, at step 510, a linear prediction model may be generated based on the received template data 318, such as the user-specific model and at step 512, line spectral frequencies may be determined based on the linear prediction model. These line spectral frequencies may then be used by to determine the frequencies for use in the subsequent biometric process.

In some embodiments, the template data related to the user may be analysed to identify frequency components that, if included in an acoustic stimulus, would contribute to discriminating the user from other users (e.g. imposters). Such frequencies can then be used as the basis for generating the acoustic stimulus as described below from step 406.

To do so, in some embodiments, a ratio herein referred to as an "F-ratio" may be defined as:

$$F\text{-ratio} = \frac{\text{inter-user feature variation}}{\text{intra-user feature variation}}$$

Where the inter-user feature variation is the variation between user features in general population or a subset of the population. The intra-user feature variation is the variation between features associated with a specific user. The intra-user feature variation may occur due to various factors such as but not limited to ear infections, personal device fit variations (such as insertion depth and leakage), device orientation, etc. As template data is received from the user, for example, due to new instances of biometric enrolment or authentication undertaken by the user, the intra-user feature variation can be updated. In doing so, the inter-user feature variation may also be updated. The F-ratio may be calculated for the entire frequency spectrum of a proposed acoustic stimulus. The frequencies that show higher F-ratio value (i.e. less inter-user variation) can be provided with larger weightings so as to provide authentication performance that is more robust to intra-user variability. Additionally or alternatively, the F-ratio may be calculated for each frequency bin of the acoustic stimulus. Each frequency bin may then be weighted as a function of the calculated F-ratio, which may be determined dynamically as new data is received regarding the user and/or the population subset.

In some embodiments, instead of generating a linear prediction model, spectrally significant components of the biometric template data 318 received at step 502B may be selected using an auto regressive moving average (ARMA) model, or any other method operable to extract or identify frequency components which might illicit ear canal responses at discriminatory frequencies useful in a biometric process.

In a variation that represents a combination of the two implementations described in FIGS. 5a and 5b, the model received at step 402A of FIG. 5a may be augmented based on user-specific data and the user augmented model used to generate the GMM at steps 502 to 508. For example, an acoustic stimulus may be generated based on data from the subset of the population. The acoustic stimulus may then be refined as more user specific data is provided to the control module 302.

In another variation of the above, steps 402 and 404 may be skipped and instead the process 400 may receive frequencies for use in the biometric process and continue to step 406.

Referring again to FIG. 4, having determined the stimulation frequencies for use in ear biometrics at step 404, at step 406, the control module 302 may then group the stimulation frequencies into bands on a psycho-acoustic scale. The psycho-acoustic scale may be a bark scale or an equivalent rectangular bandwidth (ERB) scale or a mel scale or a logarithmic scale or an octave scale. Grouping may comprise determining which bands of the psycho-acoustic scale the determined frequencies fall within.

At step 408, an acoustic stimulus may then be generated having a frequency component in each of the bands which the determined stimulation frequencies fall within. Such frequency components may be referred to herein as masked bandpass components. For example, at step 408A the acoustic stimulus may comprise a bandpass signal at each of the chosen bands. For example, the acoustic stimulus may comprise a tone at a centre frequency of each of the psychoacoustic bands in which the determined stimulation frequencies. Additionally or alternatively, the acoustic stimulus may comprise sub-band noise spanning the bandwidth of the corresponding psychoacoustic bands. Each bandpass signal may comprise all of the determined stimulation frequencies that are grouped in the corresponding psychoacoustic band. The resultant acoustic stimulus thus comprises a frequency component at each of the predicted modes of the ear canal, either of the subset of the general population or of the specific user (such as an enrolled user of the system 300).

In preferred embodiments, to further strengthen the spectral content in the acoustic stimulus, at step 408B additional frequency components may be added in each band adjacent to the chosen bands at which the determined stimulation frequencies were grouped at step 406. Such additional frequency components may be referred to herein as adjacent content. The masked bandpass content generated at step 408 above has the effect of masking this additional adjacent band content. Again, the acoustic stimulus may comprise a bandpass signal at each of the adjacent bands. For example, the acoustic stimulus may comprise a tone at a centre frequency of each of the bands adjacent to each psychoacoustic bands in which the determined stimulation frequencies and/or a sub-band noise signal spanning the bandwidth of the adjacent bands. Spectral content added in this manner to adjacent bands is likely to be masked by the content added to the acoustic stimulus at step 408A.

In some embodiments, the level of both the masked bandpass components and the adjacent content may be set, for example, to achieve high signal to noise ratio (SNR) in any ear canal response, whilst ensuring masking of content added to the acoustic stimulus. For example, at step 410, the level of each of the masked bandpass component and each adjacent component may be determined. This determination may be frequency specific or general across the entire frequency range of the acoustic stimulus. This determination may be based on an expected SNR of the ear response to the acoustic stimulus. Additionally or alternatively, a determination of level of each of the masked bandpass components and the adjacent components may be set based on playback signal information. Playback signal information may pertain to other audio which may be output or due to be output to the transducer 306 of the system 300, for example. Additionally or alternatively the determination may be made based on a prevailing background noise condition, for example by spectral analysis of ambient noise. For example, the determination may be made based on a spectral shape of ambient noise. The control module may perform such analysis based on signals derived from one or more external or reference microphones located on the personal audio device 202. Additionally or alternatively, a determination of the level may be made based on a measured level of noise leakage into an ear canal of a user. For example, where the personal audio device 202 is an earphone such as that shown in FIGS. 1c and 1c, noise leakage may be less than if the personal audio device is a handset as shown in FIG. 1e.

The time duration for application of one or more of the masked bandpass signals and/or the adjacent content may be determined at step 412. For example, for each band of the psychoacoustic scale, the time duration associated with the frequency component added to that band may be determined. Such a determination may be subject, based on an expected perceptual pleasantness of the generated acoustic stimulus. It will be appreciated that ambient noise affects the quality of ear biometric processes in which an acoustic stimulus is applied to the ear of a user and an ear canal response is received at a microphone or similar transducer. In higher background/ambient noise conditions, it may be preferable to increase the time duration of one or more of the bandpass signals. Accordingly, in some embodiments, the time duration for one or more of the bandpass signals may be set or varied in dependence on a background or ambient noise, for example as received at the transducer 316 of the system 300. This determination may be made band by band based on background or ambient noise levels in each band. As such, some of the bandpass signals may have a longer duration than others. In other embodiments, a duration may be determined for the entire signal, i.e. all bands based on the ambient or background signal level. In some embodiments, the time duration may be set based on a signal-to-noise ratio (SNR), such as the SNR of each psychoacoustic band, and/or the associated impact on or relationship to the estimation of the ear canal response. The SNR may be estimated by measuring the signal level when the acoustic stimulus is not being output to a transducer, such as the transducer 306, in addition to measuring the signal level when an acoustic stimulus is being output to the transducer 306.

Additionally or alternatively, two or more of the masked bandpass components of the signal may be temporally ordered (i.e. not temporally aligned). For example, at step 414, a temporal order may be determined for two or more of the masked bandpass components. The temporal order may be chosen to improve the listenability and/or perceptual pleasantness of the acoustic stimulus when applied to a user's ear. In some embodiments, two or more masked bandpass components may be placed in frequency order temporally, either in ascending frequency or descending frequency, for example as a function of the centre frequency of each sub-band. In some embodiments, two or more masked bandpass components may be ordered randomly. The temporal ordering of the various components may be based on a subjective analysis of perceptual pleasantness. The masked bandpass components together with the adjacent content may then be temporally ordered based on the determination at step 412. Preferably, an alignment is maintained between the adjacent content (if applied) and each of the masked bandpass components to which the adjacent content pertains.

Optionally, at step 416, one or more of the psychoacoustic bands may be filled with masked white noise or wideband stationary noise, that is noise having a flat frequency response, at a low enough level to be masked by the masked bandpass components and or the adjacent content. The provisions of this additional low energy white noise may further increase the SNR or an ear canal response to the acoustic stimulus when applied to a user's ear. As such more spectral modes in the range of interest for biometrics are excited and the convergence speed of any ear canal response estimation algorithm implemented by the system 300 is not substantially hampered by the use of a non-white noise probe signal.

Optionally at step 418, one or more comfort signals may be added to the acoustic stimulus. Such comfort signals may comprise one or more of random tones, music, triad progressions, arpeggios and the like. In some embodiments, the comfort signals may comprise a voice call signal, or a hearing augmentation signal, or a passthrough (i.e. transparency) audio signal, or an audio signal notifying the user when a device is placed in or on the user's ear. The comfort signals may be chosen to improve the listenability and/or perceptual pleasantness of the acoustic stimulus when applied to a user's ear.

The resultant acoustic stimulus generated by the control module 302 may be output to the stimulus generator module 303 at step 420 which may in turn output the stimulus to the transducer 306 during a biometric process (such as biometric enrolment or authentication).

Figure 7:
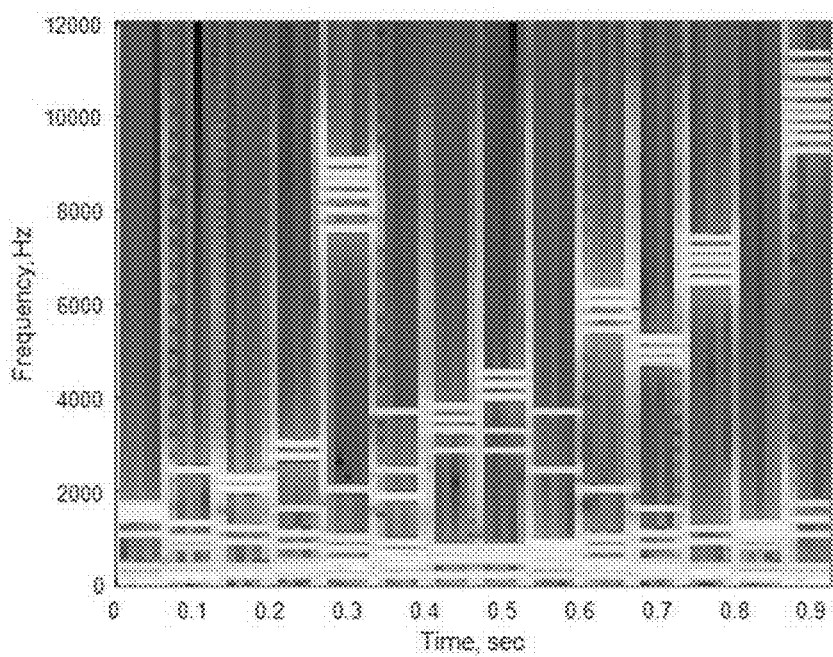
FIG. 7 is a spectrogram of an acoustic stimulus.
Figure 8:
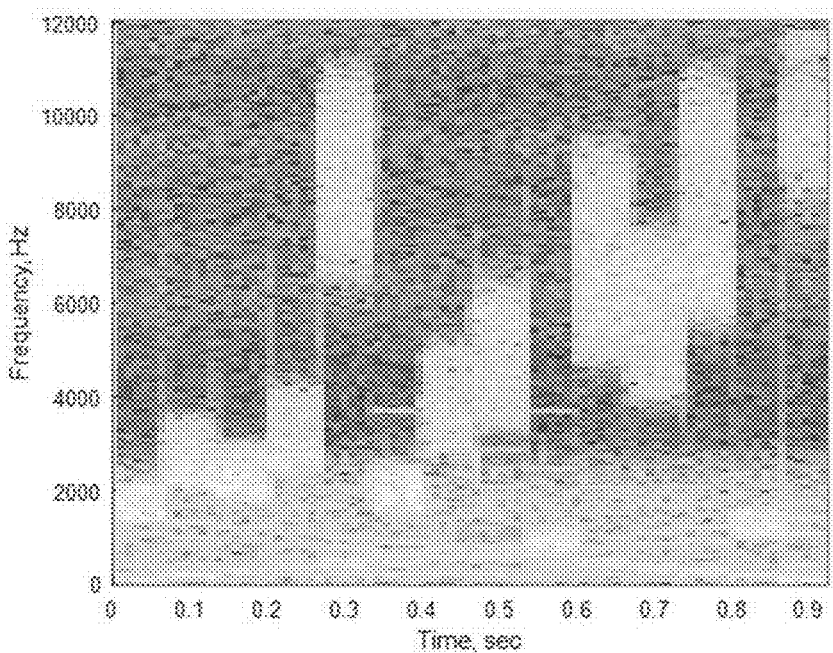
FIG. 8 is a spectrogram of an acoustic stimulus according to embodiments of the disclosure.

FIG. 7 is a spectrogram of state-of-the-art acoustic stimulus comprising a tonal chime. FIG. 8 is a spectrogram of an acoustic stimulus comprising the tonal chime having undergone spectral enriching in accordance with embodiments of the present disclosure. It can be seen that elements of the tonal chime of the acoustic stimulus in FIG. 8 are still visible and, as such, will be audible to a user when applied to the ear of the user, e.g. via the transducer 306 while the additional content will be mostly imperceptible to the user due to masking.

Figure 9:
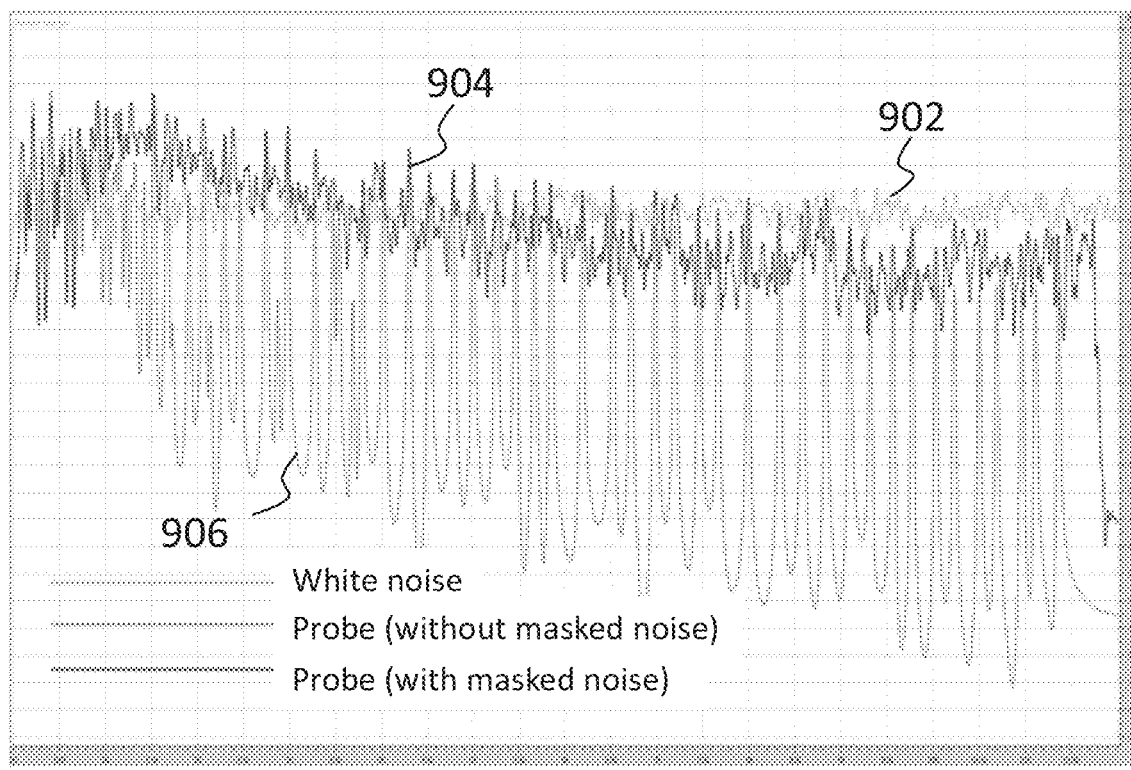
FIG. 9 is a graph showing spectrums of white noise as well as the acoustic stimuli shown in FIGS. 7 and 8.

FIG. 9 is a graph showing the magnitude spectrum between 0 Hz and 12 kHz of white noise 902, the acoustic stimulus shown in FIG. 7 (without added masked noise) and the acoustic stimulus shown in FIG. 8 (with added masked noise). It can be seen that the frequency response of the original probe signal (without added masked noise) varies dramatically across the frequency spectrum. The frequency response of the acoustic stimulus with added masked noise is relatively flat in comparison. Thus the acoustic stimulus generated in accordance with embodiments of this disclosure performs substantially similarly to white noise in biometric processes. Accordingly, whilst providing a comparatively pleasant experience for a user to which the stimulus is applied, enrolment and authentication performance is substantially maintained.

Figure 10:
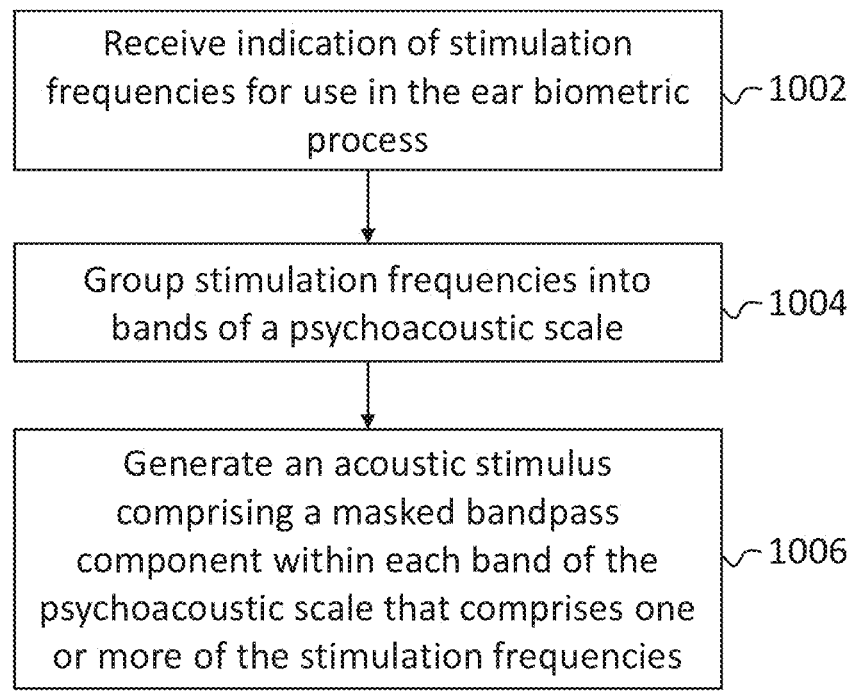
FIG. 10 illustrates a method according to embodiments of the disclosure.

FIG. 10 is a flow diagram depicting a method for generating an acoustic stimulus for use in an ear biometric process on a user in accordance with various embodiments of the disclosure.

At step 1002, an indication of stimulation frequencies for use in an ear biometric process may be received. The indication may be generated, for example, using methods described above with reference to FIGS. 4, 5*a* and 5*b*.

At step 1004, the stimulation frequencies may be grouped into bands of a psychoacoustic scale. Such grouping may be performed, for example, using the method described above in relation to step 406 of the process 400 shown in FIG. 4.

At step 1006, an acoustic stimulus may then be generated comprising a masked bandpass component within each band of the psychoacoustic scale that comprises one or more of the stimulation frequencies received at step 1002. The acoustic stimulus may be generated as described at step 408A of the process 400 shown in FIG. 4.

The skilled person will recognise that some aspects of the above-described apparatus and methods may be embodied as processor control code, for example on a non-volatile carrier medium such as a disk, CD- or DVD-ROM, programmed memory such as read only memory (Firmware), or on a data carrier such as an optical or electrical signal carrier. For many applications embodiments of the invention will be implemented on a DSP (Digital Signal Processor), ASIC (Application Specific Integrated Circuit) or FPGA (Field Programmable Gate Array). Thus the code may comprise conventional program code or microcode or, for example code for setting up or controlling an ASIC or FPGA. The code may also comprise code for dynamically configuring re-configurable apparatus such as re-programmable logic gate arrays. Similarly the code may comprise code for a hardware description language such as Verilog TM or VHDL (Very high speed integrated circuit Hardware Description Language). As the skilled person will appreciate, the code may be distributed between a plurality of coupled components in communication with one another. Where appropriate, the embodiments may also be implemented using code running on a field-(re)programmable analogue array or similar device in order to configure analogue hardware.

Note that as used herein the term module shall be used to refer to a functional unit or block which may be implemented at least partly by dedicated hardware components such as custom defined circuitry and/or at least partly be implemented by one or more software processors or appropriate code running on a suitable general purpose processor or the like. A module may itself comprise other modules or functional units. A module may be provided by multiple components or sub-modules which need not be co-located and could be provided on different integrated circuits and/or running on different processors.

Embodiments may be implemented in a host device, especially a portable and/or battery powered host device such as a mobile computing device for example a laptop or tablet computer, a games console, a remote control device, a home automation controller or a domestic appliance including a domestic temperature or lighting control system, a toy, a machine such as a robot, an audio player, a video player, or a mobile telephone for example a smartphone.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

The invention claimed is:

1. A method for generating an acoustic stimulus for use in an ear biometric process on a user, the method comprising:
   receiving an indication of stimulation frequencies for use in the ear biometric process;
   grouping the stimulation frequencies into bands of a psychoacoustic scale;
   generating the acoustic stimulus, the acoustic stimulus comprising a masked bandpass component within each band of the psychoacoustic scale that comprises one or more of the stimulation frequencies.

2. The method of claim 1, wherein the indication of frequencies is extracted from a model generated from one or more ear canal frequency responses.

3. The method of claim 2, wherein the model is a generic model generated from an analysis of ear canal frequency responses from a subset of the general population.

4. The method of claim 2, wherein the model is a user-specific model generated from an analysis of an ear canal frequency response of the user.

5. The method of claim 2, wherein frequencies in the indication of frequencies align with ear canal acoustic modes in the one or more ear canal frequency responses.

6. The method of claim 1, wherein the psychoacoustic scale comprises a bark scale or an equivalent rectangular bandwidth, ERB, scale or a mel scale or a logarithmic scale or an octave scale.

7. The method of claim 1, wherein the acoustic stimulus further comprises one or more adjacent masked bandpass components within adjacent bands of the psychoacoustic scale, the adjacent bands being adjacent to bands of the psychoacoustic scale that comprises one or more of the stimulation frequencies.

8. The method of claim 1, further comprising determining a time duration for each of the masked bandpass components.

9. The method of claim 8, wherein the time duration is determined for each masked bandpass components based on the ambient noise level in a respective band of the psychoacoustic scale.

10. The method of claim 1, wherein one or more of the masked bandpass components are temporally ordered with respect to each other.

11. The method of claim 10, further comprising varying the temporal order to reduce perceptual intrusiveness of the acoustic stimulus to a user.

12. The method of claim 1, wherein generating the acoustic stimulus comprises:
generating each of the masked bandpass components; and
combining the masked band pass components to generate the acoustic stimulus.

13. The method of claim 1, further comprising determining a signal level of each of the masked bandpass components based on one or more of:
a) an expected signal-to-noise ratio (SNR);
b) a measured ambient noise level;
c) a spectral shape of ambient background noise;
d) a measured level of noise leakage into an ear canal of the user; and
e) playback signal information.

14. The method of claim 1, further comprising combining the acoustic stimulus with a comfort stimulus.

15. The method of claim 14, wherein the comfort stimulus comprises one or more of:
a) one or more random tones;
b) music;
c) one or more triad progressions;
d) one or more arpeggios;
e) a voice call signal;
f) a hearing augmentation signal;
g) a passthrough audio signal; and
h) an audio signal notifying the user when a device is placed in or on the user's ear.

16. The method of claim 1, further comprising adding white noise to the acoustic stimulus.

17. The method of claim 1, further comprising applying the acoustic stimulus to the ear canal of a user.

18. A non-transitory machine-readable medium storing instructions which, when executed by one or more processors, cause an electronic apparatus to perform a method comprising:
receiving an indication of stimulation frequencies for use in the ear biometric process;
grouping the stimulation frequencies into bands of a psychoacoustic scale; and
generating the acoustic stimulus, the acoustic stimulus comprising a masked bandpass component within each band of the psychoacoustic scale that comprises one or more of the stimulation frequencies.

19. An apparatus comprising processing circuitry and a non-transitory machine-readable medium storing instructions which, when executed by the processing circuitry, cause the apparatus to:
receive an indication of stimulation frequencies for use in the ear biometric process;
group the stimulation frequencies into bands of a psychoacoustic scale;
generate the acoustic stimulus, the acoustic stimulus comprising a masked bandpass component within each band of the psychoacoustic scale that comprises one or more of the stimulation frequencies.

20. An electronic device comprising the apparatus of claim 19.

* * * * *

UNITED STATES PATENT AND TRADEMARK OFFICE
CERTIFICATE OF CORRECTION

PATENT NO. : 11,183,205 B1
APPLICATION NO. : 17/074776
DATED : November 23, 2021
INVENTOR(S) : Ebenezer et al.

It is certified that error appears in the above-identified patent and that said Letters Patent is hereby corrected as shown below:

In the Specification

1. In Column 7, Line 42, delete "1 e." and insert -- 1e. --, therefor.

2. In Column 9, Line 30, delete "analogue-to-digital converter (ADC) 332" and insert -- analogue-to-digital converter (ADC) 310 --, therefor.

3. In Column 9, Line 55, delete "biometric 316" and insert -- biometric module 316 --, therefor.

4. In Column 10, Line 43, delete "stimulus generator 303" and insert -- stimulus generator module 303 --, therefor.

5. In Column 10, Line 49, delete "generate" and insert -- generating --, therefor.

6. In Column 11, Line 60, delete "defined as" and insert -- defined as: --, therefor.

7. In Column 13, Line 46, delete "user specific" and insert -- user-specific --, therefor.

8. In Column 14, Line 57, delete "FIGS. 1c and 1c," and insert -- FIGS. 1c and 1d, --, therefor.

9. In Column 15, Line 8, delete "transducer 316" and insert -- transducer 306 --, therefor.

10. In Column 15, Line 48, delete "and or" and insert -- and/or --, therefor.

In the Claims

11. In Column 19, Line 2, in Claim 9, delete "each masked" and insert -- each of the masked --, therefor.

12. In Column 20, Line 16, in Claim 18, delete "the acoustic stimulus," and insert -- an acoustic Signed and Sealed this
Twenty-ninth Day of August, 2023

Katherine Kelly Vidal
*Director of the United States Patent and Trademark Office*

CERTIFICATE OF CORRECTION (continued)
U.S. Pat. No. 11,183,205 B1 stimulus, --, therefor.

13. In Column 20, Line 28, in Claim 19, delete "the acoustic stimulus," and insert -- an acoustic stimulus, --, therefor.